(12) United States Patent
Ellis et al.

(10) Patent No.: US 6,362,353 B1
(45) Date of Patent: Mar. 26, 2002

(54) MANUFACTURE OF FATTY ACID ESTERS OF SORBITAN AS SURFACTANTS

(75) Inventors: James Morgan Hunter Ellis; Jeremy James Lewis, both of Cleveland; Roger James Beattie, Tyne & Wear, all of (GB)

(73) Assignee: Imperial Chemical Industries PLC, London (GB)

( * ) Notice: Subject to any disclaimer, the term of this patent is extended or adjusted under 35 U.S.C. 154(b) by 0 days.

(21) Appl. No.: 09/230,645

(22) PCT Filed: Jul. 30, 1997

(86) PCT No.: PCT/GB97/02047

§ 371 Date: Apr. 22, 1999

§ 102(e) Date: Apr. 22, 1999

(87) PCT Pub. No.: WO98/04540

PCT Pub. Date: Feb. 5, 1998

(30) Foreign Application Priority Data

Jul. 31, 1996 (EP) .............................................. 9616034

(51) Int. Cl.$^7$ ................................................ C11C 3/00
(52) U.S. Cl. .......................................................... 554/167
(58) Field of Search ......................................... 554/167

(56) References Cited

FOREIGN PATENT DOCUMENTS

| WO | 92 00947 | 1/1992 |
|---|---|---|
| WO | 92/00947 | * 1/1992 |

OTHER PUBLICATIONS

Database WPI Week 8731 Derwent Publication Ltd., London, GB; AN 87–216863 XP002045081 & JP 62 142 141 A (Nippon Oils & Fats Co. Ltd) Jun. 25, 1987 cited in the application see abstract.

Database WPI Week 8546 Derwent Publication Ltd., London, GB; AN 85–287139 XP002045082 & JP 60 197 666 A (Sanyo Chem Ind Ltd) Oct. 7, 1985 see abstract.

* cited by examiner

*Primary Examiner*—Deborah D. Carr
(74) *Attorney, Agent, or Firm*—Pillsbury Winthrop LLP

(57) ABSTRACT

Fatty acid sorbitan esters by direct reaction of sorbitol with fatty acid using a phosphorus oxyacid, including reducing phosphorus oxyacid particulary phosphouous acid, catalyst system and an alkali or alkali earth metal base, particulaly oxide, hydroxide or carbonate, in an axid:base molar ratio of 0.9:1 to 1.7:1, at a calalust concentration of 1.5 to 30%, particularly 3 to 12%, by weight of sorbitol can have lower color than products of prior commercial bulk processes even without the use of activated carbon and product bleaching typically used previously. The esters can be further reacted with alkylene oxide to make desivatives, particularly polysorbates. The esters and polyalkyleneoxy detivatives are useful surfactants in various application. Products of low color made without using activated carbon or bleaching are attractive for personal care applications.

15 Claims, No Drawings

MANUFACTURE OF FATTY ACID ESTERS OF SORBITAN AS SURFACTANTS

This application is a 371 PCT/GB97/02047 filed Jul. 30, 1997.

This invention relates to an improved method of making surfactant esters, especially sorbitan esters of fatty acids, to the use of the product esters as surfactants, and to the manufacture of alkoxylated, especially ethoxylated, surfactant esters, in particular the ethoxylated sorbitan fatty acid esters known as polysorbates and to the use of the product alkoxylated esters as surfactants.

Sorbitan esters of fatty acids, such as those sold by various ICI companies under the Trade Mark "Span" are widely used as surfactants and as intermediates in the manufacture of relatively more hydrophilic surfactants by alkoxylation, especially ethoxylation to make so-called polysorbate surfactants e.g. as sold by various ICI companies under the Trade Mark "Tween" Typically, sorbitan fatty acid esters are commercially manufactured of a large scale by reacting sorbitol and the fatty acid in the presence of a catalyst system which promotes the esterification reaction and which also catalyses the internal etherification of the sorbitol to sorbitan. Generally the etherifcation reaction is desired only to progress to the mono-cyclic product although a second internal etherification reaction is possible to form the iso-sorbide moiety. It is believed that the internal etherification takes place after the esterification reaction, but this is not directly important for most large scale manufacturing methods as the reactions are, in practice, carried out batchwise under a single stage or "one pot" protocol. As there are various sites for esterification and internal etherification, the product is usually a mixture of isomers. Further scope for variability in the molecule is provided by the possibility of multiple esterification. The variability of the molecules possible is well known among those who manufacture and use these surfactants.

Esterification is, in principle subject to both general acid and base catalysis and etherification is typically catalysed by acids. Typically, in the manufacture of sorbitan fatty acids esters, the catalyst systems used are a mixture of acidic and basic catalysts. Conventionally explained, the base is used to catalyse the esterification and the acid to catalyse the etherification. With water being present in the system, either from supply of starting materials as aqueous solutions or water formed during the reactions, as expected, the acid and base tend to react to form salts. This may imply that the true catalyst is a salt or combination or acid or base and salt. Typically the reaction temperature is about 240° C., the catalysts are chosen so that they are both chemically stable and non-volatile at the reaction temperatures. Usually conventional catalyst systems use NaOH as the base and a phosphorus oxyacid as the acid. Various phosphorus oxyacids can be used successfully as acid components of the catalyst system, but usually non-condensed phosphorus oxyacids such as phosphoric acid have been preferred historically. Conventionally, the base and acid catalyst components (for a typical NaOH/phosphoric acid system) are used at a weight ratio of about 1:1 corresponding to a molar ratio of about 1.3:1 and at an overall level of between 0.6 and 0.8% by weight of the combined acid and sorbitol reagents equivalent to between about 2.3 and about 3% by weight of the sorbitol reagent.

At the elevated reaction temperatures typically used in the reaction, care needs to be taken to avoid excessive oxidation of the reagents and usually the reaction vessel is blanketed with nitrogen. Despite this some oxidation and/or pyrolysis (possibly oxidative pyrolysis) does usually take place and efforts have been made to reduce the extent and/or effect of these undesired side reactions on the properties of the product. The most obvious effect on the product is that it is typically coloured. Improvements in the process to reduce or remove the coloured side products include the inclusion in the reaction of carbon ("activated carbon") to absorb coloured side products and the use of reducing varieties of phosphorus acids, particularly phosphorous and/or hypophosphorous acids, to make the reaction environment less oxidising (possibly by the reducing acid acting as a sacrificial anti-oxidant). Often after separation of the activated carbon from the reaction product the product is further decolourised by bleaching. Even using such improvements, the colour of the usually liquid product (as the neat material) is typically about 8 Gardner units having a dark brown colour. In the absence of such process improvements the colour would probably be more than 10 Gardner units. Gardener units are based on visual comparisons and in this context probably represent an approximately logarithmic scale of concentration of the coloured side products.

It is known to make very pure sorbitan fatty acid esters by using specially purified starting materials and separating the etherification and esterification reactions for example as is described in JP 62-142141 A. However, such methods are of little use in the bulk manufacture of sorbitan fatty acid esters as the multiplicity of purification and reaction stages makes them very expensive.

Polyalkoxylated sorbitan fatty acid ester surfactants, particularly of the polysorbate type, are typically manufactured by reacting the corresponding sorbitan esters with alkylene oxide, usually ethylene oxide, typically under alkali catalysis.

The present invention is based on the discovery that the use of a catalyst system in which the relative proportion of acid is greater than that used conventionally can yield sorbitan fatty acid ester products which have significantly improved purity, particularly improved colour (lower Gardner colour) and odour even when no activated carbon is included in the reaction system. Further, using such modified catalyst systems enables a higher level of catalyst to be used giving shorter reaction times, lower reaction temperatures or a combination of both, which can yield further improvements in the properties of the product. The fatty acid esters can be alkoxylated, and in particularly ethoxylated to give polysorbate type products, also showing improved colour and odour as compared with otherwise similar products made with conventionally made sorbitan fatty acid esters.

Accordingly, the present invention provides a method of making fatty acid esters of sorbitan which comprises reacting the fatty acid directly with sorbitol in the presence of a catalyst system which comprises a phosphorus oxyacid, including a reducing phosphorus oxyacid, and an alkali or alkali earth metal strong base in a molar ratio of acid to base of from 0.9:1 to 1.7:1 and at a catalyst system concentration of from about 1.5 to about 30% by weight of the sorbitol.

The invention further enables the manufacture of alkoxylated esters of sorbitan, in particular polysorbate materials, having improved properties and the invention accordingly includes the use of fatty acid esters of sorbitan made by the method of the invention in the manufacture of corresponding alkoxylated esters of sorbitan, in particular polysorbate materials, by alkoxylating and in particular ethoxylating the fatty acid esters of sorbitan made according to the invention. Specifically, the invention includes a method of making alkoxylated esters of sorbitan, in particular polysorbate materials, comprising reacting a fatty acid directly with sorbitol in the presence of a catalyst system which comprises a phosphorus oxyacid, including a reducing phosphorus oxyacid, and an alkali or alkali earth metal strong base in a molar ratio of acid to base of from 0.9:1 to 1.7:1 and at a catalyst system concentration of from about 1.5 to about 30% by weight of the sorbitol to form a fatty acid ester of sorbitol; and subsequently alkoxylating, and in particular ethoxylating, the fatty acid ester of sorbitol by reacting the ester with an alkylene oxide, particularly ethylene oxide.

Molar ratios of acid and base refer to the ratios of the nominal $H^+$ and $OH^-$ content of the compounds concerned (and are thus in effect equivalent ratios of the respective acids and bases).

These ratios for phosphorus oxyacids take account of the multiple possible protons available so that e.g. phosphorus acid is treated as a dibasic acid.

The catalyst system used in the method of making fatty acid esters of the invention is a combination of an alkali or alkali earth metal strong base and an acid. The base is a strong base and will usually be an alkali or alkali earth metal oxide, hydroxide or carbonate, desirably an alkali metal hydroxide, particularly sodium and/or potassium hydroxide. The acid part of the catalyst system includes a phosphorus oxyacid. Desirably, as typical reaction temperatures are elevated, the acid catalyst is not volatile at reaction temperature and typically the acid part of the catalyst system will be wholly of phosphorus oxyacids. The phosphorus oxyacid part of the catalyst includes at least some reducing phosphorus oxyacid(s) i.e. a phosphorus oxyacid that acts as a reducing agent under the esterification reaction conditions. Desirably the reducing phosphorus oxyacid includes hypophosphorous acid and/or, and especially, phosphorous acid. We have found that phosphorous acid is much more effective than hypophosphorous acid, although the reason for this is not clear. The whole of the phosphorus oxyacid desirably is reducing acid, especially phosphorous acid, but it may be a combination of a reducing phosphorus oxyacid and one or more non reducing phosphorus oxyacid(s) particularly phosphoric acid. If such a combination is used then desirably the proportion of reduced phosphorus oxyacid, especially phosphorous acid, is at least 5%, but usually at least 25%, particularly at least 50, and typically up to 95% of the total phosphorus oxyacid.

The use of alkali metal hydroxide and phosphorous acid in the catalyst system forms a specific feature of the invention which accordingly includes a method of making fatty acid esters of sorbitan which comprises reacting the fatty acid directly with sorbitol in the presence of a catalyst system which comprises phosphorous acid and an alkali metal hydroxide in a molar ratio of phosphorous acid to alkali metal hydroxide of from 0.9:1 to 1.7:1 and at a catalyst system concentration of from about 1.5 to about 30% by weight of the sorbitol.

The molar ratio of acid: base in the catalyst system used in making fatty acid esters according to this invention is in the range 0.9:1 to 1.7:1, more usually 1:1 to 1.5:1, desirably 1.1:1 to 1.3:1 and particularly about 1.2:1. In addition to an improvement of the colour of the fatty acid ester product from the use of the particular ratios of acid to base according to the invention, we have found that this catalyst system can be a more active catalyst, speeding the reaction compared with conventional catalyst systems. The reaction to make fatty acid esters can be yet further accelerated by using higher levels of catalyst than are conventional without causing more coloration of the product. We have obtained particularly good results using up to about 6, particularly up to about 5 times and especially up to about 3 times the amount (typically about 2.3% by weight) of catalyst based on the sorbitol that is conventional. Thus in this invention the amount of catalyst used is from about 1.5 to about 30%, particularly from about 3 to about 12% and especially about 3 to about 8% by weight of the catalyst system based on the sorbitol. The catalyst concentrations are expressed based on the weight of sorbitol because this avoids apparent discrepancies arising from the differing molecular weights when different fatty acids are used and compensates somewhat for the relatively lower amounts of catalyst (based on the reaction mixture as a whole) typically used in making higher sorbitan esters e.g. sorbitan tri-fatty acid esters.

The discoloration of sorbitan fatty acid esters during manufacture is a function of the susceptibility of the fatty acid used to oxidation during the esterification/etherification process. Thus, it is well known that commercial grades of sorbitan mono-oleate tends to be more darkly coloured than the corresponding grades of sorbitan mono-stearate and this seems to flow from the unsaturation of oleic acid. The invention is particularly applicable to making esters of unsaturated fatty acids, but can be used with advantage in making saturated fatty acid esters although the relative improvement in colour is likely to be less than with unsaturated acids such as oleic acid. Typical fatty acids that can be used in the method of this invention include unsaturated fatty acids such as: oleic, linoleic, linolenic and erucic acids, and saturated acids such as lauric, myristic, palmitic stearic and behenic acids. Such fatty acids are commonly available as mixtures of fatty acids of similar carbon chain length which are as found in the natural source from which they are obtained (or as mimicked by synthetic analogues), for example coconut fatty acids (COFA)—mainly a mixture of $C_{12}$ and $C_{14}$ acids, palm oil fatty acids—mainly palmitic acid and hydrogenated tallow fatty acids—mainly stearic acid. Such mixtures can readily be used as the fatty acid source in the method of this invention.

The grade of sorbitol used can also affect the colour of the fatty acid ester product. The use of a grade with low content of reducing i.e. aldehyde or ketone containing, sugars is desirable as the carbonyl groups are recognised as likely to be relatively easily converted to coloured products on pyrolysis, especially oxidative pyrolysis. However, the method of making fatty acid esters according to this invention can give substantial benefits even with grades of sorbitol that are not especially low in reducing sugars. In the method of the invention, the colour of the product can be improved modestly by the inclusion of metabisulphite e.g. as sodium metabisulphite added as a solid or as an aqueous solution, in the reaction mixture. We believe that the improvement arising from the inclusion of metabisulphite arises from the formation of a metabisulphite adduct with the aldehyde or ketone groups of reducing sugars thus reducing the susceptibility of the system towards colour formation during the reaction to make the fatty acid ester. The amount of metabisulphite used will typically be from 0.1 to 10% by weight of the sorbitol, the amount generally corresponding to the level of reducing sugars in the sorbitol. This addition can give a benefit of about 0.5 to 1 Gardner unit of colour in the product fatty acid ester.

The intended fatty acid ester product can be a mono-, or higher ester as there are nominally four free hydroxyl groups in sorbitan. Typically mono-, sesqui-, di- and tri-fatty acid esters of sorbitan are made commercially and similar product can be made by the method of this invention. In practice the products are made to meet a performance specification as they are commercial materials and although they are often named using terms suggesting relatively precise compounds, the products will often have non-integral ratios of sorbitan and fatty acid residues. For example, commonly the product sold as sorbitan mono-oleate will contain on average from 1.4 to 1.5 oleic acid residues per sorbitan residue. With this in mind, for the lower esters the fatty acid and sorbitol will typically be used in approximately equimolar proportions and the reaction will proceed substantially to completion. Where higher esters are desired, some of the fatty acid may not react with the sorbitan and will remain as (nominally) free acid in the synthesis product. Thus, nominal sorbitan tri-oleate typically contains about 10% unreacted oleic acid.

The method of this invention can produce fatty acid ester products, without the use of activated carbon, with a colour superior to that obtained by otherwise similar prior art processes including the use of activated carbon. The use of activated carbon is not excluded in this invention, but its inclusion does not appear to give any significant further benefit. Indeed avoiding the use of activated carbon may be advantageous as it is difficult or messy to filter from the fatty acid ester reaction product and tends to retain some of the product, typically amounting to a few percent of the total yield, in the filter in a form that is not readily separable from the carbon.

Similarly, in typical prior art processes, to obtain product with a (then relatively) low colour, the fatty acid ester product would typically be bleached e.g. with hydrogen peroxide. In this invention, products with good colour can be obtained without bleaching. Even further improved colour can be obtained by bleaching the product of this invention. However, particularly for personal care applications, it can be desirable to use non-bleached fatty acid ester products as this obviates any risk of including bleach residues or side products from bleaching in the final products.

The reaction to make the fatty acid esters is typically carried out in an inert atmosphere, usually under a nitrogen blanket, to minimise oxidative degradation of the starting materials or products, and at a temperature sufficiently high to drive off water present in the starting materials or generated by the etherification and esterification reactions. Typically, the reaction mixture is heated to the maximum intended reaction temperature after mixing of the reagents and addition of the catalyst. Conventional maximum reaction temperatures are typically about 240 to 250° C., but we have found that lower reaction temperatures can be used. Thus, in this invention the peak reaction temperature will typically be in the range 150 to 250° C. but more usually from 170 to 230° C. The use of reaction temperatures lower than those that are conventional is particularly appropriate where increased concentrations of catalyst are used. At catalyst levels 2 to 3 time conventional levels, the reaction temperature can be in the range 200 to 230° C. and by using higher levels of catalyst e.g. up to about 6 times the conventional level the reaction temperature can be reduced to about 170° C. if desired. The reduction in reaction temperatures seems to provide a further benefit in the colour and purity of the product. Even with relatively low reaction temperatures, the reaction times using the method of this invention can be shorter than is conventional. We have obtained satisfactory conversion in a reaction time of 5 hours at a peak reaction temperature of 220° C. as compared with a reaction time of 8 hours with a peak reaction temperature of 245° C. using a more nearly conventional type of catalyst system (ca. 1.3:1 molar sodium hydroxide: phosphorous acid at 0.7% by weight).

The lower colour fatty acid ester products which can be made by the method of this invention makes them particularly suitable for inclusion as dispersants and/or emulsifiers in personal care products. Specific end uses are generally associated with particular esters so that sorbitan palmitate, stearate and behenate are particularly useful in oil-in-water creams, milks and lotions with a wide range of end use applications; the iso-stearate and oleate in water-in-oil creams, milks and lotions and bath and massage oils, water washable ointments and in decorative cosmetics, particularly lipsticks, blushers and other make up items, especially as pigment dispersants; and laurate in mudpacks, particularly as dispersants, and in baby shampoos, particularly as conditioners.

In addition to the advantage of lower colour, the sorbitan fatty acid esters made by the method of this invention have less odour, and usually a less objectionable odour, than conventional materials. Thus, the odour is typically more akin to that of toffee than the burnt or rancid odours associated with conventional sorbitan esters as currently commercially available. A further advantage, of particular relevance to their use in personal care products, is that esters made by the method of this invention need not and generally will not include residues of bleaching materials because bleaching materials are not used (because as described above they are not necessary). This may make these materials particularly attractive for personal care products, such as cosmetics, that are used for long periods in contact with skin.

The invention accordingly includes personal care products, particularly of the types mentioned above, including one or more fatty acid ester compound(s) made by the method of the invention as a dispersants and/or emulsifiers and the use of fatty acid ester compounds made by the method of the invention as a dispersants andlor emulsifiers in personal care products.

The improvement in colour and odour also makes it possible to make alkoxylated products, particularly ethoxylated products of the polysorbate type, of improved colour and odour and as noted above the invention includes the manufacture of alkoxylated, particularly ethoxylated, sorbitan fatty acid esters and the use of sorbitan fatty acid esters made by the method of the invention in the manufacture of alkoxylated, particularly ethoxylated, sorbitan fatty acid esters (polysorbates). The alkoxylation reaction on the sorbitan ester is typically carried out at superambient temperatures e.g. from about 125 to 175° C., typically using a basic catalyst, usually an alkali metal hydroxide such as usually sodium or potassium hydroxide or alkali metal fatty acid salts. The reaction is continued until the desired degree of alkoxylation, usually expressed as a OH number (mg KOH equivalent per gram of product), is reached. At the end of the reaction the basic catalyst is neutralised to give an unbleached product. The improved colour of the sorbitan fatty acid esters may make it possible to omit the normal post-alkoxylation bleaching step in the manufacture of such alkoxylated products and this is a particularly advantage for personal care products where bleaching residues are required to be minimised (and are desirably absent). The improvement in odour is also relevant for personal care and food additive uses of such materials. If a product having even lower colour is desired then the alkoxylated material may be bleached conventionally e.g. with hydrogen peroxide.

Such alkoxylated, particularly ethoxylated derivatives of sorbitan esters are used as emulsifiers and dispersants in oil-in-water emulsions and creams and in particular as soublisers for perfumes and flavouring materials in personal care and food products.

The invention accordingly further includes personal care products and food product and/or additives, particularly of the types mentioned above, including one or more alkoxylated, particularly ethoxylated, sorbitan fatty acid ester(s) made by the method of the invention as dispersants and/or emulsifiers and/or solublisers; and the use of alkoxylated, particularly ethoxylated, sorbitan fatty acid ester(s) made by the method of the invention as a dispersants and/or emulsifiers and/or solublisers in personal care and/or food and/or food additive products.

The improved colour sorbitan esters and aikoxylated, especially ethoxylated sorbitan esters, made according to this invention may be susceptible to an increase in colour on storage, particularly if special care is not taken. To make the products less likely to deteriorate for this reason it may be desirable to include a small proportion e.g. 0.01 to 0.25% by weight of an antioxidant such as 2,6-di-tert-butyl4-methylphenol in the ester products.

The following Examples illustrate the invention. All parts and percentages are by weight unless otherwise specified.

| Materials Used | |
|---|---|
| oleic acid | Priolene 6900 ex Unichema |
| lauric acid | nominal lauric acid was COFA - fatty acids derived from coconut oil (a mixture of C12 to C14 mainly saturated fatty acids) |
| sorbitol | Sorbidex 130 ex Cerestar |
| Dicalite | a diatomaceous earth filter aid ex Redland Minerals |
| Test Methods | |
| colour | was measured using a Gardner Colorimeter and the results are expressed in Gardner units (GU). |
| acid number | was measured by the method of ASTM D974-92 and the results are expressed in mg(KOH equivalent).g(sample)$^{-1}$. |
| hydroxyl number | was measured by the method of ASTM E326-85 and the results are expressed in mg(KOH equivalent).g(sample)$^{-1}$. |
| saponification no | was measured by the method of CAPAR4/1 and the results are expressed in mg(KOH equivalent).g(sample)$^{-1}$. |

EXAMPLE 1

The laboratory scale esterification reactor used was a 1 l flat flanged glass flask fitted with a nitrogen supply, thermometer (thermocouple), a mechanical p.t.f.e. stirrer a Vigreaux column having a side arm condenser leading to a collection flask and an external isomantle. Oleic acid (416 g; 1.47 mol), sorbitol (184 g; 1 mol; as a 70% aqueous solution) and catalyst (4.8 g; 2.6% by weight based on the sorbitol of a mixture of NaOH and phosphorous acid in a molar ratio of acid:base of 1.2:1) were charged to the flask, the mix was thoroughly sparged with nitrogen (and throughout the reaction) and the temperature increased steadily to 110° C. when water (from the sorbitol solution) started to distil from the reaction mixture. The temperature was increased slowly to 130° C. until the removal of free water was nearly complete and was then increased to 245° C. over 30 minutes. The reaction was monitored by periodic sampling and analysis for acid number until this fell below 10 and then by hydroxyl number until this dropped within the range 210 to 185. The amount of water distilled from the reaction was also used as an indication of the extent or the reaction. The reaction mix was then filtered through a medium flow filter paper using 1% by weight (based on the weight of the reaction mixture) Dicalite as filter aid. This Example was repeated except that the catalyst used was 2.3% by weight of a mixture of NaOH and phosphorous acid in a molar ratio of acid:base of 0.8:1 as comparative Example 1C. The properties of these products were as follows:

| property | Ex 1 | Ex 1C | Units |
|---|---|---|---|
| acid number | 3.3 | 24 | mg(KOH).g$^{-1}$ |
| hydroxyl number | 199 | 193 | mg(KOH).g$^{-1}$ |
| saponification no | 154 | 152 | mg(KOH).g$^{-1}$ |
| colour | 3.5 | 7 | Gardner units |

EXAMPLES 2 TO 9

Example 1 was repeated using various molar ratios of acid to base and varying amounts of catalyst. The ratios and amounts and the effect on the colour of the product is set out in Table 1 below which includes data from further comparative examples 2C to 4C. In comparative Example 4C the acid used was phosphoric acid i.e. no reducing phosphorus oxyacid was used.

EXAMPLE 10

Example 1 was repeated except that the molar ratio of oleic acid to sorbitan used was about 3:1 to make (nominal) sorbitan trioleate and that the amount of catalyst used was 5.7% by weight of the sorbitol at an acid to base molar ratio of 1.2:1. Comparative Example 10C is similar to Example 10 but used a molar ratio of acid to base of 0.8:1 at a level of about 2.8%. The results are included in Table 1 below.

EXAMPLE 11

Example 1 was repeated except that the oleic acid used in Example 1 was replaced with lauric acid (COFA) and that the amount of catalyst used was 3.2% by weight at an acid to base molar ratio of 1.2:1. Comparative Example 11C is similar to Example 11 but used a molar ratio of acid to base of 0.8:1 at a catalyst level of 1.6%. The results are included in Table 1 below.

EXAMPLE 12

Example 5 was repeated except that activated carbon (6.7 g; 1.8% by weight) was included in the the product was 3 GU, the same as that of Example 5.

EXAMPLE 13

Example 7 was repeated except that sodium metabisulphite (0.1 g; 1.8% by weight based on the reaction mix. The colour of the product was 2.5 GU, an improvement Example 7.

EXAMPLE 14

Example 7 was repeated except that hypophosphorous acid (0.26% by weight, giving a molar ratio of acid:base of 1.2:1 was used instead of the phosphorous acid used in Example 7. The colour of the product was 5 Gu 2 GU worse than the product of Example 7.

TABLE 1

| Ex No | Fatty Acid | Catalyst Wt % | Catalyst molar ratio | Colour (GU) |
|---|---|---|---|---|
| 1 | oleic | 2.6 | 1.2 | 3.5 |
| 1C | oleic | 2.3 | 0.8 | 7 |
| 2 | oleic | 2.3 | 0.9 | 5 |
| 3 | oleic | 3 | 1.5 | 5 |
| 4 | oleic | 4.3 | 1.2 | 3.5 |
| 5 | oleic | 2.3 | 1.2 | 3 |
| 2C | oleic | 2.3 | 0.8 | 6 |
| 6 | oleic | 7.6 | 1.1 | 3 |
| 7 | oleic | 8.2 | 1.2 | 3 |
| 8 | oleic | 8.6 | 1.4 | 4 |
| 3C | oleic | 6.6 | 0.8 | 6 |
| 9 | oleic | 9.9 | 1.7 | 5 |
| 4C | oleic | 8.2 | 1.2 | 7 |
| 10 | oleic x3 | 5.7 | 1.2 | 5 |
| 10C | oleic x3 | 2.8 | 0.8 | 9 |
| 11 | lauric | 3.2 | 1.2 | 2–3 |
| 11C | lauric | 1.6 | 0.8 | 6 |

EXAMPLE 15

Example 4 was repeated in a pilot scale reactor to produce about 25 kg of ester product. At the end of the esterification the colour of the product was 5 GU. Procedurally the ester was held in the reaction vessel under nitrogen for an extended period at the end of which the colour had increased to 8 GU (because of further degradation reactions during the holding period).

EXAMPLE 16

A sample of the product of Example 15 was ethoxylated in a 19 l pilot autoclave reactor fitted with a paddle overhead agitator. Sorbitan mono-oleate (ca 1500 g; ca 3.4 mol) was charged to the reactor and was deaerated under vacuum at ambient temperature. The temperature was increased to 90° C. and sodium hydroxide catalyst added. The mix was heated further to 120° C. and water removed under vacuum. Ethylene oxide gas (ca 2990 g; ca 68 mol) was added over maintaining a constant pressure of ca 5 bar until the hydroxyl value of the product indicated near completion of the reaction, and the system allowed to react after completion of the ethylene oxide addition until the pressure fell to a constant level. The ethoxylated product was then cooled to and vacuum stripped maintaining the temperature above 100° C., further cooled and acid added to neutralise the catalyst. This unbleached ethoxylate had a colour of 7 GU. Correcting the colour of this product to offset the higher colour of the ester (from the holding time at elevated temperature) gives a value of about 3.5 to 4 GU.

The effect of bleaching this product was investigated by bleaching a sample with hydrogen peroxide at 90° C. This bleached product had a colour of 5 GU. Correcting the colour of this product to offset the higher colour of the ester (from the holding time at elevated temperature) gives a value of about 2 to 3 GU.

A comparative run was also carried out under the conditions of Example 16 starting with commercially available sorbitan mono-oleate (Span 80 ex ICI Surfactants) having a colour of 8 GU. the unbleached ethoxylate had a colour of about 6 to 7 GU and the bleached ethoxylate about 5.5 GU.

What is claimed is:

1. A method of making fatty acid esters of sorbitan which comprises reacting the fatty acid directly with sorbitol in the presence of a catalyst system which comprises a phosphorus oxyacid, including a reducing phosphorus oxyacid, and an alkali or alkali earth metal strong base in a molar ratio of acid to base of from 0.9:1 to 1.7:1 and at a catalyst system concentration of from about 1.5 to about 30% by weight of the sorbitol.

2. A method as claimed in claim 1 wherein the reducing phosphorus oxyacid is or includes phosphorous acid.

3. A method as claimed in claim 1 wherein the base component of the catalyst system is an alkali or alkali earth metal oxide, hydroxide or carbonate.

4. A method as claimed in claim 3 wherein the base is sodium and/or potassium hydroxide.

5. A method as claimed in claim 1 wherein the catalyst system which comprises phosphorous acid and an alkali metal hydroxide in a molar ratio of phosphorous acid to alkali metal hydroxide of from 0.9:1 to 1.7:1 and at a catalyst system concentration of from about 1.5 to about 30% by weight of the sorbitol.

6. A method as claimed in claim 1 wherein in the catalyst system, the ratio of acid:base is in the range 0.9:1 to 1.7:1.

7. A method as claimed in claim 6 wherein the ratio of acid:base is in the range 1.1:1 to 1.3:1.

8. A method as claimed in claim 1 wherein the catalyst system concentration is from about 3 to about 12% by weight based on the sorbitol.

9. A method as claimed in claim 8 wherein the catalyst system concentration is about 3 to about 8% by weight based on the sorbitol.

10. A method as claimed in claim 1 wherein the reaction mixture additionally includes a metabisulphite.

11. A method as claimed in claim 8 wherein the metabisulphite is sodium metabisulphite.

12. A method as claimed in claim 10 wherein the amount of metabisulphite used is from 0.1 to 10% by weight of the sorbitol.

13. A method as claimed in claim 1 in which the reaction is carried out at a temperature in the range 170 to 230° C.

14. A method of making an alkoxylated ester of sorbitan made by the method claimed in claim 1 which comprises reacting the ester with an alkylene oxide.

15. A method as claimed in claim 14 wherein the alkylene oxide is ethylene oxide.

* * * * *